(12) United States Patent
Vedantham et al.

(10) Patent No.: US 8,817,947 B2
(45) Date of Patent: Aug. 26, 2014

(54) TOMOSYNTHESIS IMAGING

(75) Inventors: Srinivasan Vedantham, Holden, MA (US); Andrew Karellas, Grafton, MA (US)

(73) Assignee: University of Massachusetts, Boston, MA (US)

( * ) Notice: Subject to any disclaimer, the term of this patent is extended or adjusted under 35 U.S.C. 154(b) by 386 days.

(21) Appl. No.: 13/360,128

(22) Filed: Jan. 27, 2012

(65) Prior Publication Data

US 2012/0195403 A1 Aug. 2, 2012

Related U.S. Application Data

(60) Provisional application No. 61/437,749, filed on Jan. 31, 2011.

(51) Int. Cl.
*A61B 6/00* (2006.01)
*A61B 6/02* (2006.01)

(52) U.S. Cl.
CPC ............... *A61B 6/022* (2013.01); *A61B 6/502* (2013.01); *A61B 6/4007* (2013.01)
USPC .............................................. 378/21; 378/37

(58) Field of Classification Search
CPC ...... A61B 6/022; A61B 6/025; A61B 6/4007; A61B 6/502
USPC ......................................... 378/21–27, 37, 41
See application file for complete search history.

(56) References Cited

U.S. PATENT DOCUMENTS

| | | | |
|---|---|---|---|
| 6,649,914 B1 | 11/2003 | Moorman et al. | |
| 6,980,624 B2 | 12/2005 | Li et al. | |
| 7,099,435 B2 | 8/2006 | Heumann | |
| 7,330,529 B2 | 2/2008 | Kautzer et al. | |
| 7,545,907 B2 | 6/2009 | Stewart | |
| 7,551,716 B2 | 6/2009 | Ruhrnschopf | |
| 7,616,801 B2 | 11/2009 | Gkanatsios et al. | |
| 7,680,240 B2 | 3/2010 | Manjeshwar | |
| 7,697,661 B2 | 4/2010 | Souchay et al. | |
| 7,702,142 B2 | 4/2010 | Ren | |
| 7,751,528 B2 | 7/2010 | Zhou | |
| 2003/0095624 A1 | 5/2003 | Eberhard | |
| 2005/0226371 A1 | 10/2005 | Kautzer et al. | |
| 2009/0268865 A1 | 10/2009 | Ren et al. | |
| 2009/0304147 A1 | 12/2009 | Jing et al. | |
| 2010/0063410 A1 | 3/2010 | Avila | |
| 2010/0091940 A1 | 4/2010 | Ludwig et al. | |

FOREIGN PATENT DOCUMENTS

| | | |
|---|---|---|
| EP | 1759637 A2 | 3/2007 |
| WO | 2010060007 A1 | 5/2010 |

*Primary Examiner* — Courtney Thomas
(74) *Attorney, Agent, or Firm* — Milstein Zhang & Wu LLC; Joseph B. Milstein

(57) ABSTRACT

Systems and methods for providing radiographic, stereoscopic and tomographic images of an object of interest. Examples of objects of interest are body parts of living beings, such as the human breast and the human chest. The apparatus includes a high-fluence rate x-ray source and a plurality of satellite x-ray sources operating at lower fluence rate than the high-fluence rate source. A controller controls the operation and locations of the sources, and the operation of a detector. The method provides procedures in which the operation of the high-fluence source and the satellite sources are individually controlled as to location and orientation relative to the object of interest. In some operations, one satellite source may be operating while another satellite source may be repositioning. By proper control, a reduced x-ray dose and reduced operating time can be attained, thereby improving image quality, patient care, and patient experience.

25 Claims, 7 Drawing Sheets

TOMOSYNTHESIS IMAGING

CROSS-REFERENCE TO RELATED APPLICATIONS

This application claims priority to and the benefit of U.S. provisional patent application Ser. No. 61/437,749 filed Jan. 31, 2011 which application is incorporated herein by reference in its entirety.

STATEMENT REGARDING FEDERALLY FUNDED RESEARCH OR DEVELOPMENT

This invention was made with government support under Grant Nos. CA134128, CA128906 and EB004015 awarded by the National Institutes of Health. The Government has certain rights in the invention.

FIELD OF THE INVENTION

The invention relates to x-ray-based imaging systems and methods in general and particularly to an imaging system and method that provides x-ray images.

BACKGROUND OF THE INVENTION

Digital radiography provides a two-dimensional (2-D) image of a three-dimensional (3-D) object resulting in superposition of structures. Stereoscopic imaging is a technique wherein at least two 2-D x-ray projection images, referred to as an image pair, separated by an angle not exceeding 20-degrees (typically, 3 to 10 degrees) are acquired and displayed on a stereo-capable display. Such display may include two monitors each displaying one of the projection images, and the displayed projection images are viewed through cross-polarized mirrors and lenses, resulting in one eye visualizing one image and the other eye the other image. Alternatively, the images can be visualized using "3-D displays" such as those used in consumer electronics. In typical implementation of stereoscopic imaging, the image pair is acquired by physical movement of a single x-ray tube. Digital tomosynthesis is a technique wherein a plurality of 2-D x-ray projections are acquired over a limited angular range not exceeding 180-degrees (typically, 15 to 90 degrees) and mathematically reconstructed to provide a quasi-tomographic or 3-D image of object. This technique has the potential to improve detection of an abnormality in body anatomy and is being actively investigated for breast, chest and abdominal imaging. FDA-approved clinical systems for chest imaging and for breast imaging have been developed by various manufacturers.

In typical implementation of digital tomosynthesis, (n+1) projections are acquired over an angular range of $-\theta$ to $+\theta$ spanning $2\theta$ degrees. Here n is a positive integer. Typically, the peak tube voltage (given in kilovolts peak, or kVp) applied across the anode-cathode of the x-ray tube, and the anode target and x-ray beam filter, referred to target/filter are maintained the same during acquisition of the (n+1) projections. The kVp and target/filter define the x-ray spectral shape, and in combination with the tube current (in millamps), or mAs where mAs is the product of tube current in mA and the x-ray exposure duration in seconds) define the x-ray fluence (photons per unit area). In early studies (see Niklason, L. T., B. T. Christian, L. E. Niklason, D. B. Kopans, D. E. Castleberry, B. H. OpsahlOng, C. E. Landberg, P. J. Slanetz, A. A. Giardino, R. Moore, D. Albagli, M. C. DeJule, P. F. Fitzgerald, D. F. Fobare, B. W. Giambattista, R. F. Kwasnick, J. Q. Liu, S. J. Lubowski, G. E. Possin, J. F. Richotte, C. Y. Wei, and R. F. Wirth, *Digital Tomosynthesis in breast imaging*. Radiology, 1997. 205(2): p. 399-406; Suryanarayanan, S., A. Karellas, S. Vedantham, S. P. Baker, S. J. Glick, C. J. D'Orsi, and R. L. Webber, *Evaluation of linear and nonlinear tomosynthetic reconstruction methods in digital mammography*. Acad Radiol, 2001. 8(3): p. 219-24; and Suryanarayanan, S., A. Karellas, S. Vedantham, S. J. Glick, C. J. D'Orsi, S. P. Baker, and R. L. Webber, *Comparison of tomosynthesis methods used with digital mammography*. Acad Radiol, 2000. 7(12): p. 1085-97), tube current was also maintained the same during acquisition of the (n+1) projections.

In current practice, the multiple views required for tomosynthesis require the physical rotation of the x-ray tube for each tomographic view. Although this is technically attainable, the physical movement of the tube is the source of many problems in tomosynthesis. A moving x-ray tube prolongs the exposure time and the duration of physical compression of the breast that in turn increases patient discomfort. Moreover, the resulting longer image acquisition time is more likely to contribute to blurring of the images due to patient motion and physical movement of the x-ray tube.

Systems using multiple stationary x-ray sources have been described by others for use in tomosynthesis, particularly for breast imaging (Kautzer et al. US 2005/0226371 A1 and U.S. Pat. No. 7,330,529 B2, Ludwig et al. US 2010/0091940 A1, Zhou et al. U.S. Pat. No. 7,751,528). However, such systems lack a central high power x-ray tube or other type of high-power x-ray source. A tomosynthesis system with a series of stationary sources will have no capability of performing conventional digital mammography because this requires a relatively high power x-ray source to provide sufficient x-ray fluence rate (defined as the number of x-ray photons per unit area per unit time, or x-ray fluence per unit time) that meet mammographic requirements for a reasonably short x-ray exposure, typically between 0.3 to 2.0 second duration. The fixed multi-spot x-ray sources are significantly underpowered and currently they are not capable of delivering the high x-ray fluence needed for mammography in an acceptable time frame to minimize patient motion. Therefore, such systems will be limited to tomosynthesis use only and not mammography. However, a mammographic or radiographic unit that can only operate in the tomosynthesis mode is too limited and it will not be desirable in most medical practices, because most breast imaging centers would prefer a system that can perform both tests. The same reasoning applies to digital radiography and tomosynthesis of other parts of the body such as chest, abdominal and pelvic imaging.

Some mammographic and radiographic imaging systems currently manufactured can perform conventional digital mammography and tomosynthesis on demand. In the conventional approach, tomosynthesis can be performed by a mechanical scan of the rotating anode x-ray tube over an arc of about +/−30 degrees from the center and acquiring typically from 15 to 25 images across this scan. The detector may remain stationary or it can rotate and/or move laterally to track the x-ray beam. Each of the 15 to 25 images require a combination of rapid activation of the x-ray tube (termed as "fire") followed by a mechanical movement to the next position for the next fire or x-ray source activation. This rapid firing and mechanical repositioning creates many problems that lead to a less than optimal tomosynthesis image acquisition. During each firing there is a rise and fall "pulse" of the x-ray tube voltage. The tube current and x-ray output can be hard to control without elaborate and expensive electronic controls. Any irregularities in this pulse can contribute to an increased dose to the patient particularly due to the slow rise and drop of the waveform. Moreover, the x-ray filament is susceptible to the mechanical vibrations of the movement of the tube and this can have a negative effect on the spatial resolution of images. A mechanical "stop-fire-and-go" approach is very problematic because of the mechanical instabilities due to acceleration and deceleration of the mechanical assembly of the x-ray source. Continuous mechanical movement is generally preferred but it also prone to vibrations that can affect the image quality. In addition, during each firing that is of finite duration, the x-ray tube is in continuous motion resulting in blurring that degrades image quality. It typically takes between four to ten seconds for a complete acquisition and this increases the chances for a slight movement of the breast or other part of the body that will degrade the spatial resolution and diagnostic quality of the images. This motion problem can be minimized by applying additional compression on the breast using the pneumatic compression mechanism and plate but this is highly undesirable because of increased pain or discomfort. In chest and abdominal radiography this problem is even more serious because shorter exposures are required, typically in the order of milliseconds in chest imaging. A published international patent application by Ren et al. (WO 2010/060007 A1) discusses some of the issues of mechanical scanning approaches.

Other prior art known to the inventors includes the following patents and published applications.

U.S. Pat. No. 6,649,914 issued to Moorman et al. on Nov. 18, 2003 is said to describe an x-ray imaging system according to the present invention comprising a stepped scanning-beam x-ray source and a multi-detector array.

U.S. Pat. No. 7,099,435 issued to Heumann on Aug. 29, 2006 is said to describe a tomographic reconstruction method and system incorporating Bayesian estimation techniques to inspect and classify regions of imaged objects, especially objects of the type typically found in linear, areal, or 3-dimensional arrays.

U.S. Pat. No. 7,545,907 issued to Stewart on Jun. 9, 2009 is said to describe a method of obtaining projection data of an object from a plurality of view angles with respect to the object is provided. The method comprises acts of providing radiation, at each of the plurality of view angles, to an exposure area in which the object is positioned, controlling a radiation energy of the radiation provided at each of the plurality of view angles such that the respective radiation energy is different for at least two of the plurality of view angles, and detecting at least some of the radiation passing through the exposure area at each of the plurality of view angles to obtain the projection data.

U.S. Pat. No. 7,551,716 issued to Ruhrnschopf on Jun. 23, 2009 is said to describe scatter correction methods for breast imaging and is relevant to the "scatter compensation in tomosynthesis" aspect of our disclosure. The approach described by Ruhrnschopf uses a pre-computed library of scatter spread functions using Monte Carlo simulations, which is a standard computational tool for scatter estimation. We have published previously Monte Carlo simulations of scatter as a function of tomosynthesis projection angle. See Sechopoulos, I., S. Suryanarayanan, S. Vedantham, C. J. D'Orsi, and A. Karellas, *Scatter radiation in digital tomosynthesis of the breast*. Med Phys, 2007. 34(2): p. 564-76.

U.S. Patent Application Publication No. 20090268865 A1 (Ren et al.) published on Oct. 29, 2009. This patent application is said to describe a method and an apparatus for estimating a geometric thickness of a breast in mammography/tomosynthesis or in other x-ray procedures, by imaging markers that are in the path of x-rays passing through the imaged object.

U.S. Pat. No. 7,616,801 issued to Gkanatsios et al. on Nov. 10, 2009 is said to describe a method and system for acquiring, processing, storing, and displaying x-ray mammograms Mp and tomosynthesis images Tr representative of breast slices, and x-ray tomosynthesis projection images Tp taken at different angles to a breast, where the Tr images are reconstructed from Tp images.

U.S. Patent Application Publication No. 20100063410 A1 (Avila), published Mar. 11, 2010, describes obtaining a lung cancer risk index based on combining information from multiple sources such as spirometry, chest CT or other x-ray examination including x-ray tomosynthesis with airflow lung function measurements.

U.S. Pat. No. 7,680,240 issued to Manjeshwar on Mar. 16, 2010 is said to describe methods for performing image reconstruction that include deriving background projection data for an area outside a targeted field of view of a tomographic image, and reconstructing the tomographic image of the targeted field of view, wherein the background projection data is used in the reconstruction.

U.S. Pat. No. 7,697,661 issued to Souchay et al. on Apr. 13, 2010 is said to describe a method wherein the irradiation dose to the breast is distributed in a manner based on the orientation of the x-ray beam followed by filtering of the projections to ensure optimum propagation of the signal-to-noise ratio.

U.S. Pat. No. 7,702,142 issued to Ren on Apr. 20, 2010 is said to describe a method and a system for using tomosynthesis projection images of a patient's breast to reconstruct slice tomosynthesis images such that anatomical structures that appear superimposed in a mammogram are at conforming locations in the reconstructed images.

U.S. Pat. No. 7,751,528 issued to Zhou on Jul. 6, 2010 is said to describe using a stationary array of x-ray sources to facilitate tomosynthesis.

Other references known to the inventors include the following non-patent literature: Nishikawa, R. M., I. Reiser, P. Seifi, and C. J. Vyborny, *A new approach to digital breast tomosynthesis for breast cancer screening, in Medical Imaging* 2007: *Physics of Medical Imaging*, J. Hsieh and M. J. Flynn, Editors. 2007, SPIE. p. 65103C; and Sechopoulos, I., S. Suryanarayanan, S. Vedantham, C. D'Orsi, and A. Karellas, *Computation of the glandular radiation dose in digital tomosynthesis of the breast*. Med Phys, 2007. 34(1): p. 221-32.

A number of problems in attempting to implement a method and system that provides both radiographic and tomographic images have been observed.

There is a need for methods and systems that provide radiographic, stereoscopic and tomographic images.

SUMMARY OF THE INVENTION

According to one aspect, the invention features an x-ray apparatus for making an image. The x-ray apparatus comprises an object holder configured to position an object of interest to allow the making of an image of the object; an x-ray source configured to provide a first x-ray beam having a high x-ray fluence rate to illuminate the object of interest along a first axis; at least one peripheral satellite x-ray source configured to provide at least one secondary x-ray beam having lower x-ray fluence rate than the fluence rate of the first x-ray beam, the at least one secondary x-ray beam configured to illuminate the object of interest along a respective axis that is angularly displaced from the first axis; a detector configured to detect x-ray radiation that has passed through the object of interest from the x-ray source and from the at least one peripheral satellite x-ray source, the detector having an output port configured to provide non-volatile signals representative of the detected x-ray radiation that has passed through the object of interest; a controller configured to command the operation of the x-ray source, configured to command the operation of each of the at least one peripheral satellite x-ray source, and configured to command the operation of the detector to generate the non-volatile signals representative of the detected x-ray radiation that has passed through the object of interest; and a computation unit configured to receive the non-volatile signals representative of the detected x-ray radiation from the detector and configured to manipulate the non-volatile signals representative of the detected x-ray radiation to provide at least one image of the object of interest, the computation unit configured to perform at least one action selected from the group of actions consisting of recording the image of the object of interest, displaying to a user the image of the object of interest, and transmitting the image to a data handling system.

In one embodiment, the object of interest is a body part of a living being.

In another embodiment, the body part of a living being is a human breast.

In yet another embodiment, the x-ray source and at least one peripheral satellite x-ray source are configured to be rotated as a combined unit with reference to the object of interest.

In still another embodiment, the x-ray source and at least one peripheral satellite x-ray source are configured to be positioned independently of one another with reference to the object of interest.

In a further embodiment, at least one peripheral satellite x-ray source is configured to be operated individually.

In yet a further embodiment, the detector is configured to be stationary, or is configured to rotate or move laterally to track an x-ray beam.

In an additional embodiment, the controller is configured to control a parameter selected from the group of parameters consisting of an x-ray beam energy, an x-ray beam fluence rate and an x-ray beam duration in response to an orientation of the x-ray beam.

In one more embodiment, the apparatus further comprises an anti-scatter grid located in an x-ray beam path.

In still a further embodiment, the apparatus further comprises a computational unit configured to apply an x-ray scatter correction method.

In one embodiment, at least one image of the object of interest is an image selected from the group of images consisting of a radiographic image, a stereoscopic image, and a tomographic image.

In another embodiment, the x-ray source configured to provide a first x-ray beam having a high x-ray fluence rate is a high power source.

In a further embodiment, the high power source is selected from the group of sources consisting of a rotating anode source, a high fluence field emission source, and a synchrotron.

According to another aspect, the invention relates to a method of making a plurality of images. The method comprises the steps of providing an object of interest for the purpose of making an image of the object; illuminating the object of interest with a first x-ray beam having a high x-ray fluence rate, the first x-ray beam propagating along a first axis; illuminating the object of interest with at least one secondary x-ray beam having lower x-ray fluence rate than the fluence rate of the first x-ray beam, the at least one secondary x-ray beam propagating along a respective axis that is angularly displaced from the first axis; detecting the first x-ray beam and the at least one secondary x-ray beam after they have each passed through the object of interest; generating non-volatile signals representative of the detected x-ray radiation that has passed through the object of interest; manipulating the non-volatile signals representative of the detected x-ray radiation to provide a plurality of images of the object of interest, the plurality of images comprising a stereoscopic image and at least one image selected from the group consisting of a radiographic image and a tomographic image; and performing at least one action of recording the images, transmitting the images to a data handling system, and displaying the images to a user.

In one embodiment, the step of illuminating the object of interest with a first x-ray beam, the step of illuminating the object of interest with at least one secondary x-ray beam, the step of detecting the first x-ray beam and the at least one secondary x-ray beam, and the step of generating non-volatile signals representative of the detected x-ray radiation are performed in response to commands from a controller.

In another embodiment, the step of illuminating the object of interest with a first x-ray beam and the step of illuminating the object of interest with at least one secondary x-ray beam are performed in any order.

In yet another embodiment, the step of illuminating the object of interest with at least one secondary x-ray beam includes illuminating the object of interest with a first of the at least one secondary x-ray beams in a first time interval and illuminating the object of interest with a second of the at least one secondary x-ray beams in a second time interval different from the first time interval.

In still another embodiment, the source of a first of the at least one secondary x-ray beams provides x-ray illumination while a source of a second of the at least one secondary x-ray beams is moving.

In a further embodiment, at least one of the steps of illuminating the object of interest comprises illuminating the object of interest with an x-ray beam having at least one parameter selected from the group of parameters consisting of x-ray beam energy, x-ray fluence rate and x-ray beam duration, the at least one parameter having a value that is dependent on an orientation of the x-ray beam.

In yet a further embodiment, at least one of the steps of illuminating the object of interest with at least one secondary x-ray beam is used to provide one or more of the stereoscopic image, the radiographic image and the tomographic image.

In an additional embodiment, the step of illuminating the object of interest with at least one secondary x-ray beam is used for stereotactic localization to obtain samples of the object of interest.

In one more embodiment, at least one of the steps of illuminating the object of interest comprises the steps of illuminating the object of interest with an anti-scatter grid in an x-ray beam path; illuminating the object of interest without an anti-scatter grid in the x-ray beam path, and; applying an x-ray scatter correction method comprising the steps of: estimating an x-ray scatter present in an image recorded at a first beam orientation; determining an x-ray scatter present in an image recorded at a second beam orientation different from the first beam orientation by using the estimated x-ray scatter estimated at the first beam orientation; and applying the determined x-ray scatter as a correction for x-ray scatter in an image recorded at the second beam orientation.

In still a further embodiment, the step of determining an x-ray scatter present in an image recorded at a second beam orientation is performed using Monte Carlo simulations.

In yet another embodiment, the step of determining an x-ray scatter present in an image recorded at a second beam orientation is performed using a library of data that accounts for the range of dimensions and properties of the object.

In still another embodiment, the step of applying the determined x-ray scatter as a correction is performed using at least one mathematical procedure selected from the group of mathematical procedures consisting of analytical mathematical operations, iterative mathematical operations, convolution techniques and de-convolution techniques.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Figure 1:
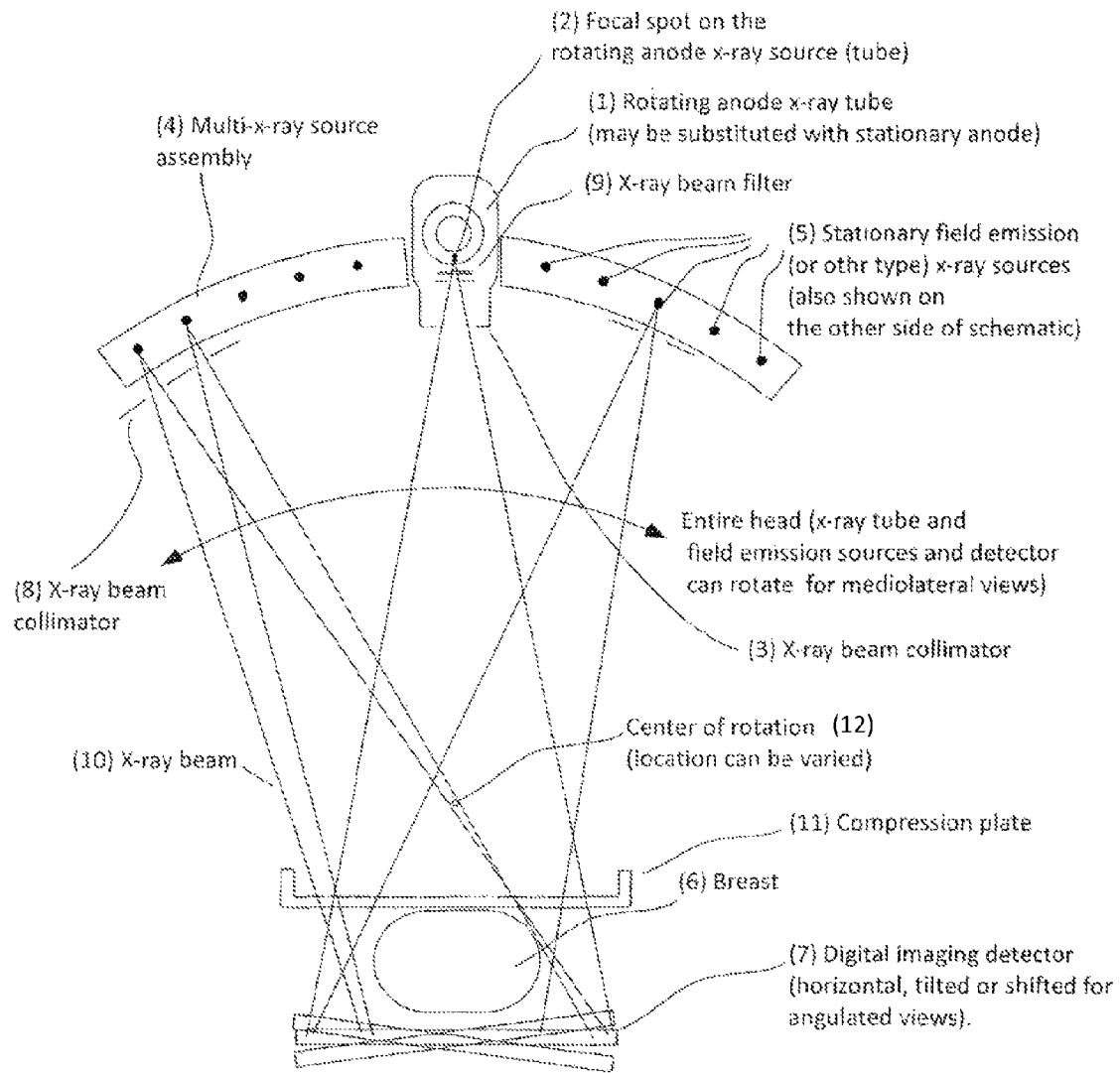
FIG. 1 is a schematic diagram that shows a system according to principles of the invention that includes a central x-ray source and satellite x-ray source assemblies.

Combined Digital Mammography with High Speed Tomosynthesis

We describe a method for tomosynthesis imaging that uses a number of x-ray sources positioned on each side (or only on one side if desired) of the conventional central x-ray tube. This preferred embodiment enables fast tomographic image acquisition for tomosynthesis and for stereoscopic x-ray imaging. Image acquisition parameters (kVp, target/filter, mAs), either individually or in combination, can be varied with projection angle during acquisition of the (n+1) projections. We refer to such variation of operating parameters as angle adaptive beam modulation (AABM).

In order to overcome the limitations of prior art systems, it is desirable and advantageous to have a series of spatially fixed x-ray sources in an arc path that can activate sequentially or in any desired order to cover the desired angle of exposure in the shortest possible time.

We describe a system that is expected to be fully capable of operating as a state-of-the art mammography or radiography system and it also is expected to be capable of operating as a high speed tomosynthesis system by using a combination of a standard high power source and a plurality of peripheral "satellite" x-ray sources. We describe using a combined stationary x-ray source array and a conventional x-ray tube. The x-ray tube can be positioned at the center of the x-ray source array. This allows the use of high x-ray fluence rate projection acquisition using the standard x-ray tube and lower x-ray fluence rate projection acquisitions using the stationary x-ray source array. The combined x-ray tube and stationary x-ray source array can be rotated with reference to an object to be examined in order to facilitate finer angular sampling of the object. Alternatively, each source array can be rotated independently. It is possible in principle to use two or more lower x-ray fluence rate projection acquisitions using the stationary x-ray source array without the high x-ray fluence rate projection to generate some of the images discussed herein below.

In various embodiments, the high power source can be a conventional rotating anode source, or a non-conventional higher power x-ray source such as a high fluence field emission source or a synchrotron for the first axis projection rather than the stationary x-ray source. While the first axis can be a central axis (e.g., at zero-degrees in reference to the central ray axis), it is not required that it be a central axis; that is the first axis can be off-center in some embodiments. The preferred embodiments described use one or more banks of stationary sources interposed with a rotating anode x-ray source or a number of lower powered sources interposed with a rotating anode x-ray source. The use of a rotating anode x-ray source is significant so as to provide sufficient x-ray output for digital mammography. Rotating anode x-ray tubes designed for mammography can provide upwards of 5 KW power (Tube voltage: 50 kV, Tube current: 100 mA), whereas stationary sources can only provide tube currents of the order of 3 to 7 mA, as described in a recent article from Zhou's research group (see Calderon-Colon, X., H. Geng, B. Gao, L. An, G. Cao, and O. Zhou, *A carbon nanotube field emission cathode with high current density and long-term stability*. Nanotechnology, 2009. 20(32): p. 325707).

Figure 2:
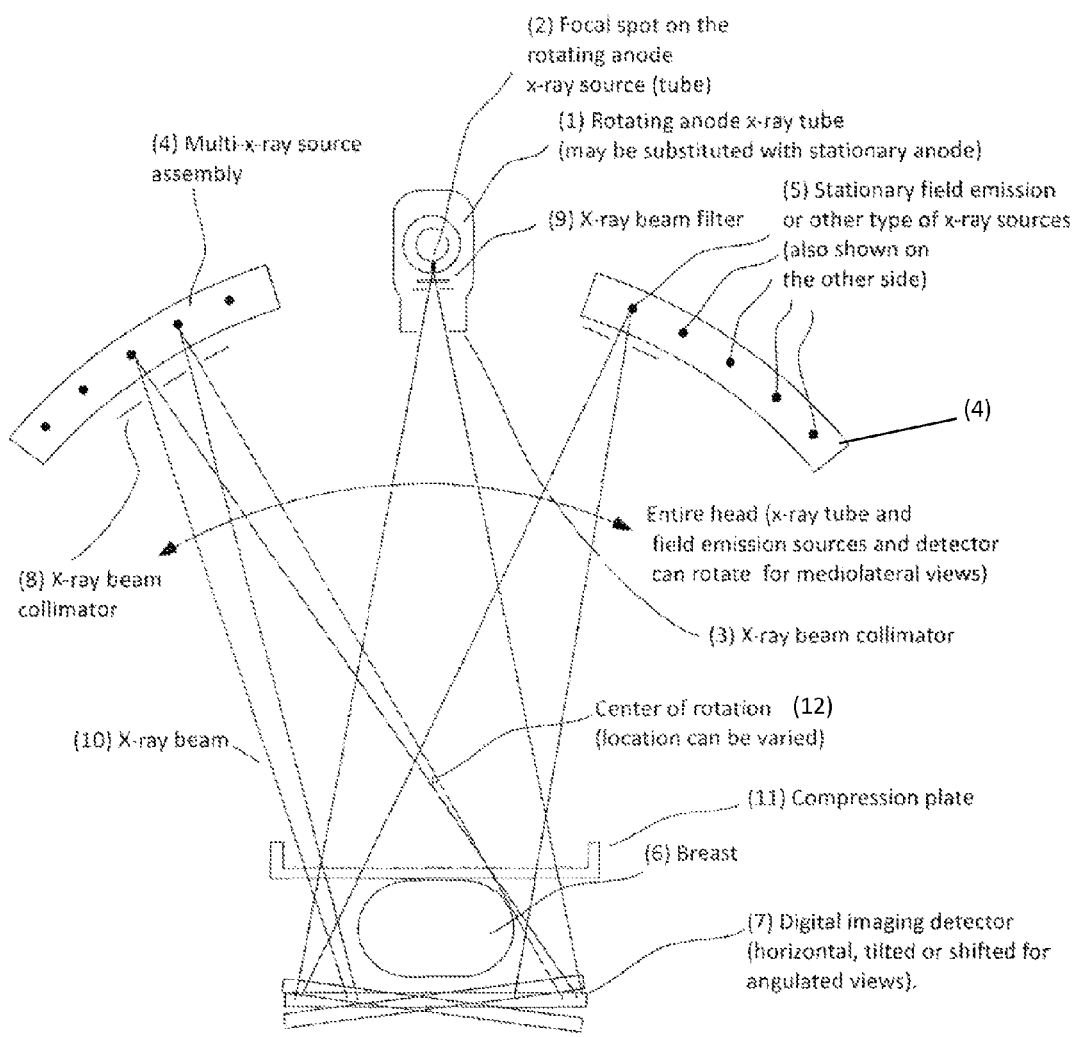
FIG. 2 is a schematic diagram that shows a variation of the described approach with the satellite x-ray source assemblies (right and left) spread in an arc away from the central x-ray source, according to principles of the invention.

We describe a dual-use mammographic and tomosynthesis system that is also capable of stereoscopic imaging and stereotactic localization and employs a conventional central x-ray source and detector with an additional set of x-ray sources (satellite sources, 4) on each side of a conventional x-ray source (1) as shown in FIG. 1 and FIG. 2. As is well-known in the x-ray imaging and tomographic imaging arts, once data is acquired using a detector, the data is manipulated in a general purpose programmable computer operating with instructions recorded in non-volatile memory accessible by and readable by the general purpose programmable computer. The images that are extracted from the acquired data can be recorded, can be transmitted to another computational system, and/or can be displayed to a user of the imaging system.

FIG. 1 is a schematic diagram that shows several important features of an embodiment of the invention. Illustrated in FIG. 1 are the elements of a digital mammography or tomosynthesis unit with a conventional x-ray tube (1), which can be a rotating anode x-ray tube or a stationary anode x-ray tube. The x-ray tube has at least one small high heat load focal spot (2). An x-ray beam collimator (3) and an x-ray beam filter (9) are provided to control the high power x-ray beam emanating from the x-ray tube (1). Also present is an x-ray source assembly (4) having a plurality of x-ray sources (5). The x-ray source assembly (4) also termed "satellite sources") is constructed of multiple segments which are movable, with a center of rotation (12) about which each of the x-ray sources (5) can be rotated. In one embodiment, the x-ray sources (5) are x-ray sources constructed using field emission x-ray sources. In other embodiments, other types of x-ray sources can be used. Multiple x-ray beam collimators (8) are provided to collimate the x-ray beam emanating from each of the x-ray sources (5). The breast (6) of a patient is illustrated under compression by a breast compression plate (11). A digital imaging detector (7) is provided to record the intensity of the x-ray beams (10) that are used to generate mammographic and tomographic images. The digital imaging detector (7) can be oriented normal to the axis of the rotating anode x-ray tube (1) or it can be tilted or shifted to provide angulated views. The digital imaging detector (7) can be made of amorphous selenium with a thin film transistor (TFT) or optical readout, or an amorphous silicon detector with a scintillator or a photon counting detector. The x-ray sources operate in a range of kVp from about 20 to 150 so that the range that is used for mammography (20 to 50 kVp) and for adult and pediatric radiography (40 to 150 kVp) can be covered.

This approach obviates the mechanical scanning of the x-ray tube to perform tomosynthesis. Conventional mammography in the craniocaudal, mediolateral and other mammographic views can be performed by rotating the tube and detector c-arm assembly as in the conventional approach. However, the tomosynthesis acquisition can be acquired by firing the satellite x-ray sources in a predetermined sequence. The satellite x-ray sources are typically of the field emission type (using carbon nanotubes or other components) and they are integrated in groups of two or more as shown in FIG. 1. One advantage of this design is the ability to fire a very rapid sequence of tomosynthesis projections without mechanical movement of the main x-ray source (tube 1). This enables a tomographic acquisition in a very short time, typically in the order of approximately one second, that represents at least a tenfold improvement over existing techniques. Moreover, the tomographic acquisition can be performed in the same sequence as the conventional view. For example, the conventional mammographic view can be acquired at a typical exposure time from about one-half second to three seconds followed by or preceded immediately by a tomographic acquisition without repositioning the breast. For chest radiography, the exposure time will be in the millisecond range, typically between 1 millisecond to 1 second. This approach enables for the visualization of conventional and tomographic images that have been acquired in the same position and they can be digitally fused for better correlation between conventional mammographic image and tomographic image acquisition. The use of multiple x-ray sources is expected to require test procedures and calibrations to minimize variation in x-ray beam quality and quantity.

FIG. 2 is a schematic diagram that shows a variation of the described approach with the satellite x-ray source assemblies (4 right and 4 left) spread in an arc away from the central x-ray source 1. In this embodiment a tomosynthesis acquisition can be made at different angles from the center. Moreover, each satellite source assembly can be positioned in a way that can be rotated independently or in synchrony with the other assembly.

Figure 3:
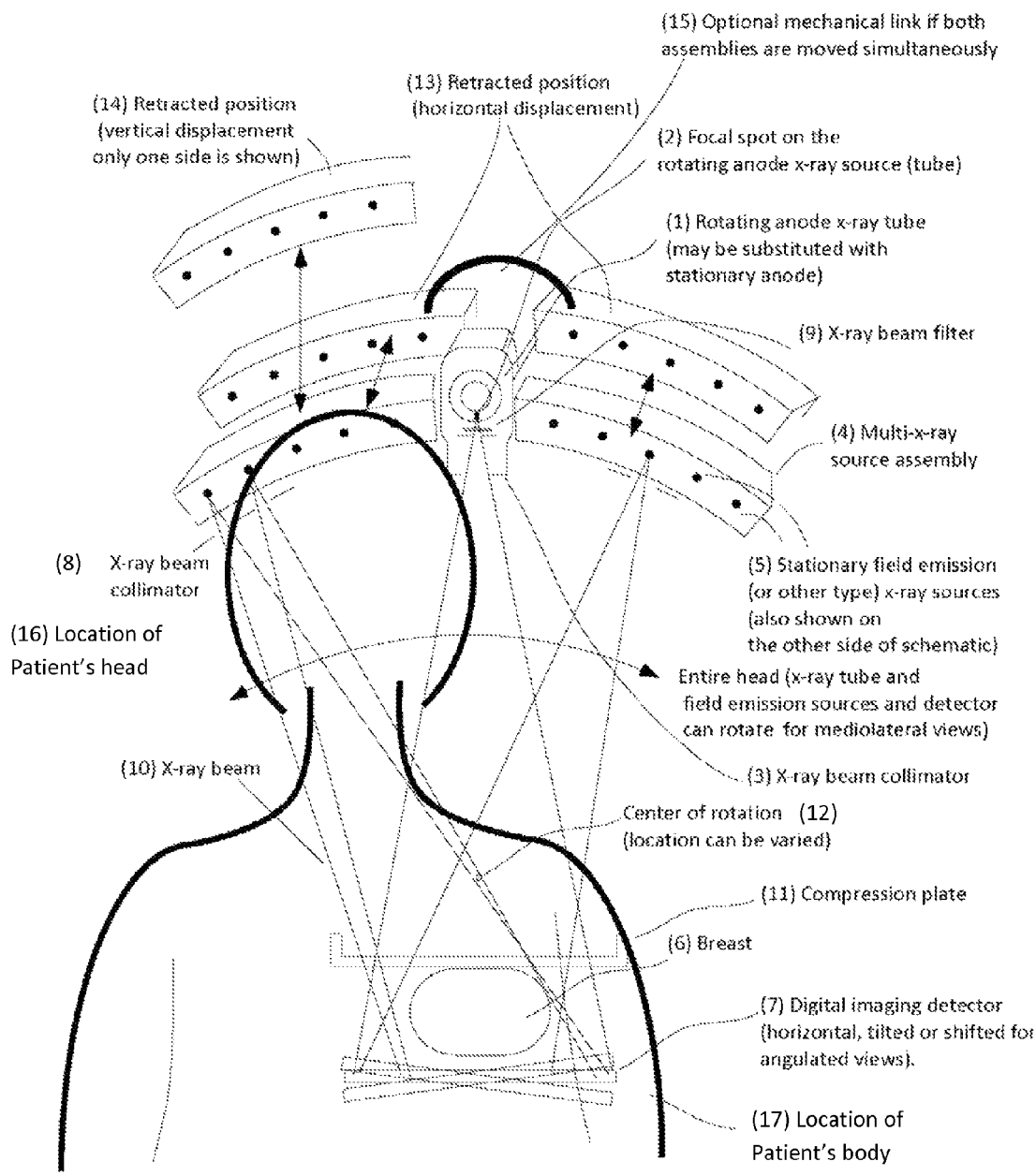
FIG. 3 is a schematic diagram that shows a variation of the described approach that is used when only a conventional mammogram is required.

FIG. 3 is a schematic diagram that shows a variation of the described approach that is used when only a conventional mammogram is required. In FIG. 3, it is shown how the satellite x-ray source assemblies (4) can be translated away from the patient (to locations 13 and/or 14 as shown) or can be tilted away from the patient, which motion is not shown. In some embodiments, the satellite x-ray source assemblies (4) can be moved individually. In some embodiments, the satellite x-ray source assemblies (4) can be moved as a unit, in which case a mechanical link (15) between the two satellite x-ray source segments can be provided. In some embodiments, mechanical detents are provided to assure that the satellite x-ray sources (4) are returned to carefully controlled positions for use in conjunction with the x-ray tube (1) as previously described. In some embodiments, locating devices such as optical, electrical or magnetic encoders are provided to assure that the satellite x-ray sources (4) are returned to carefully controlled positions for use in conjunction with the x-ray tube (1) as previously described. The ability to temporarily displace the satellite x-ray sources (4) can be helpful in improving patient positioning. Outlines of the location of a patient' head (16) and body (17) are indicated in FIG. 3.

Figure 4:
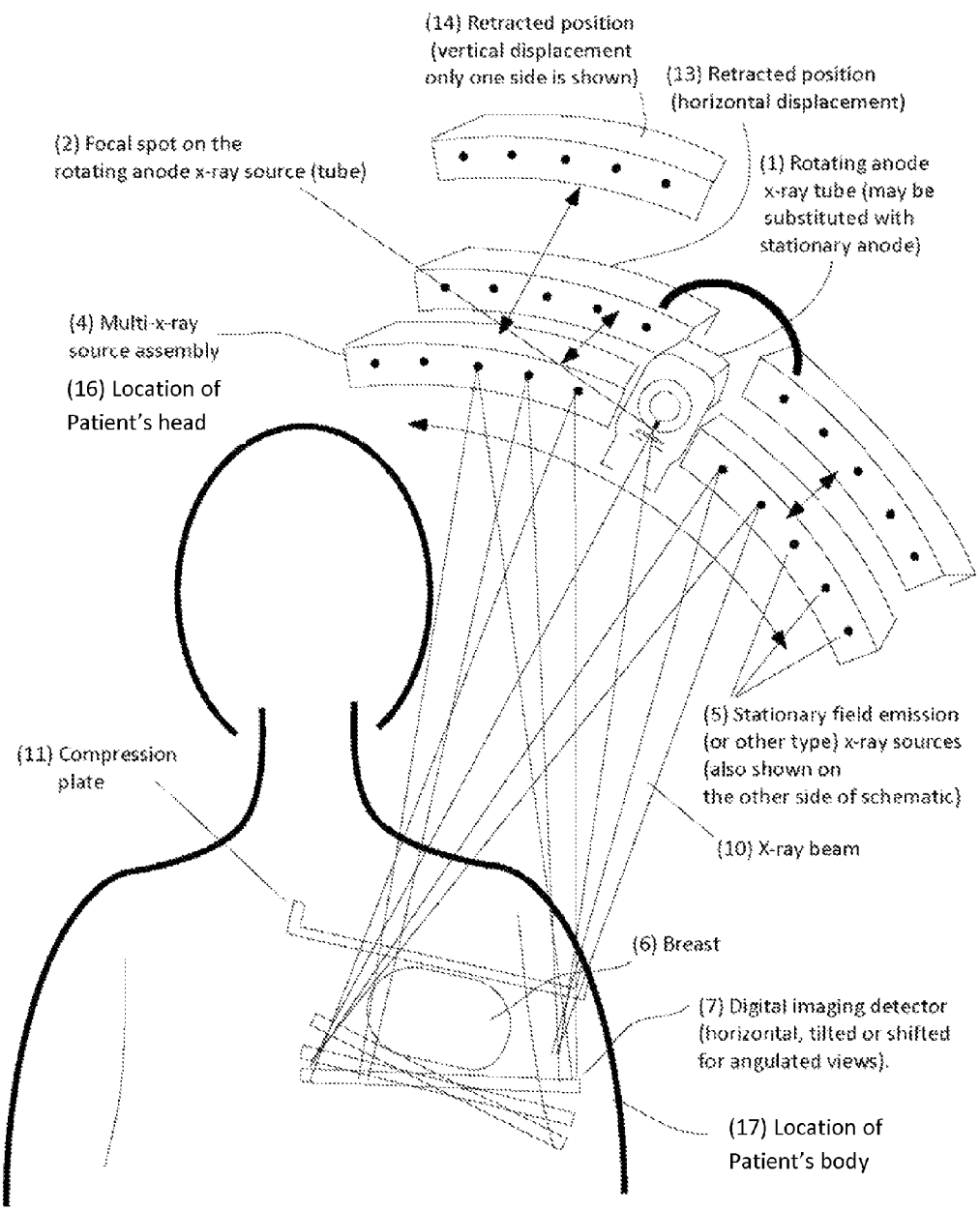
FIG. 4 is another view of the relative positions of a patient, a portion of a patient's body that is being examined, and the position of the apparatus.

FIG. 4 is another view of the relative positions of a patient, a portion of a patient's body that is being examined, and the position of the apparatus. FIG. 4 shows the satellite x-ray sources (4) in position for providing a tomography image, and in positions (locations 13 and/or 14 as shown) where the satellite x-ray sources are not expected to be used in making a tomographic image. In FIG. 4, the outline of the patient represents a patient closer to the viewer than the apparatus is to the viewer (e.g., one is looking through the patient), and the patient has her back to the viewer.

The firing of each x-ray tube can be activated in a number of ways. For example, in one mode of operation, the left source assembly can fire each source sequentially while both assemblies are positioned adjacent to the central x-ray source as shown in FIG. 1. Subsequently, the right assembly fires sequentially while the left assembly moves a predetermined distance counterclockwise (away from the central source). After firing of the selected sources is completed in the right assembly, firing of the sources starts on the left source assembly from its new position farther away from the central x-ray source (tube 1). This approach allows the combination of an electronic and mechanical positioning of the focal spot thereby allowing for speed and the ability to acquire projections from various points beyond what is dictated by the number of available satellite x-ray sources.

FIG. 1 and FIG. 2 show a symmetric positioning of the satellite x-ray sources on each side of the main x-ray source (1). In other modes of operation, an asymmetric arrangement may also be desirable. An arrangement using a central x-ray source (1) in conjunction with just two satellite sources (5) is also desirable particularly for stereo-mammography.

Figure 5:
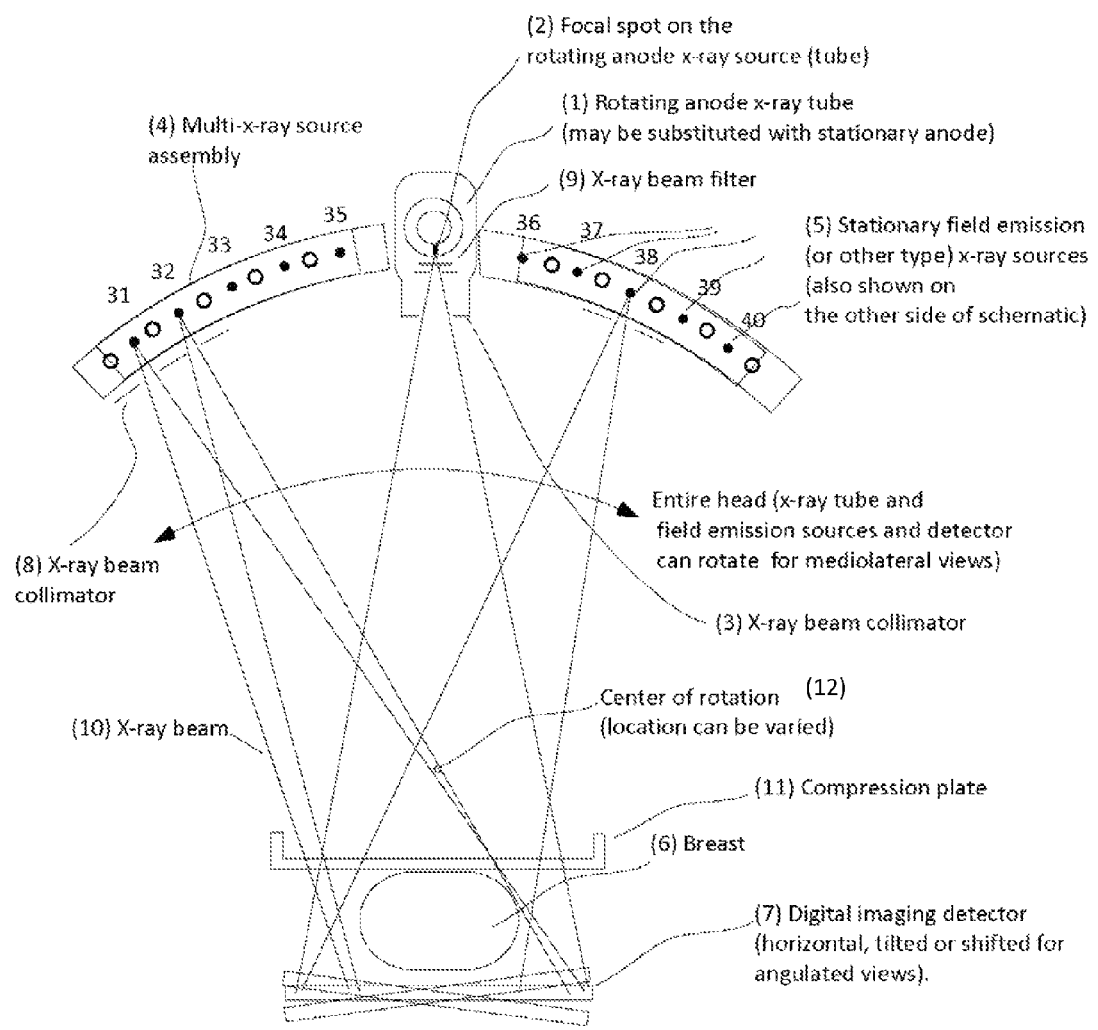
FIG. 5 is a schematic diagram that illustrates an embodiment in which the individual sources in the satellite x-ray sources are operated in sequence.

FIG. 5 is a schematic diagram that illustrates an embodiment in which the individual sources in the satellite x-ray sources (4) are operated in sequence. In FIG. 5 ten individual sources in the satellite x-ray sources (4) are represented by filled dark circles and are labeled 31 through 40. In the position illustrated, sources 31 through 35 may be fired in a desired sequence, such as in succession or in some other order. While sources 36 to 40 are being fired in the desired sequence, the segment of the satellite x-ray source containing sources 31-35 moves in a counterclockwise motion of a pre-defined number of degrees (or pre-defined in units represented by another frame of reference). After the motion is completed, the sources 31-35 are located at the positions illustrated by open circles. Sources 31-35 can then be fired again in a desired sequence, while the segment of the satellite x-ray source containing sources 36-40 moves in a clockwise motion of a pre-defined number of degrees (or pre-defined in units represented by another frame of reference) so that sources 36-40 come to be located where the corresponding open circles are illustrated. Sources 36-40 can then be fired again in a desired sequence. The movements and firings can be performed as many times as may be desirable or necessary to obtain the images that are sought.

Figure 6:
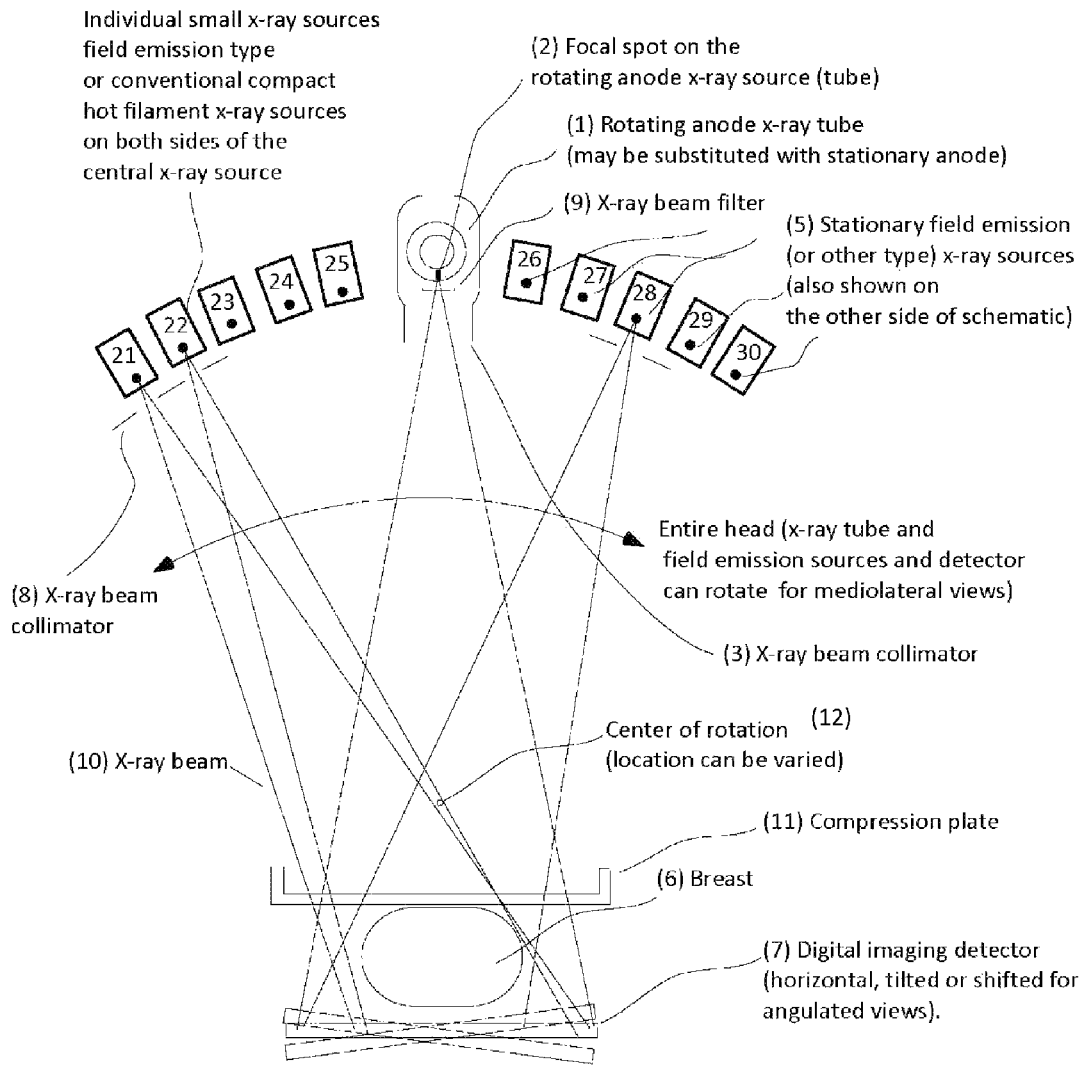
FIG. 6 is a schematic diagram that illustrates an embodiment in which the satellite x-ray sources comprise a plurality of discrete individual sources.

FIG. 6 is a schematic diagram that illustrates an embodiment in which the satellite x-ray sources comprise a plurality of discrete individual sources. In FIG. 6, ten individual sources, labeled respectively 21 through 30, are provided instead of the ten sources 31-40 illustrated in FIG. 5.

While FIG. 5 and FIG. 6 show a total of ten satellite x-ray sources as illustrative embodiments, the number of sources in a satellite x-ray source can be fewer than ten or greater than ten, as individual designs may require, or as may be found to be useful. The number ten is to be understood simply as a useful number for explanation of the apparatus and the method, and is not limiting. Any convenient number of sources can be provided in the apparatus.

Scatter Compensation in Tomosynthesis

The term "scatter" is commonly used for x-rays that are scattered in tissues and that are detected by the image receptor (the film screen or the digital detector in modern equipment). This x-ray scatter carries incorrect positional information and it degrades the contrast of radiographic images. Scatter is known to be detrimental to image quality. Aggressive measures are taken to suppress its effect in mammography and radiography by using anti-scatter grids. Software based techniques for correcting for the effects of scatter in radiographic imaging have been described. Breast and non-mammographic tomosynthesis would benefit from numerical algorithms and techniques that correct for the effects of scatter. However, such techniques will require accurate estimation of scatter that could vary substantially with each breast or other body part of a patient. However, unlike mammography and radiography, current implementations of digital tomosynthesis do not use an anti-scatter grid and they do not implement numerical scatter correction algorithms to counter the deleterious effect of x-ray scatter.

In another preferred embodiment we perform x-ray scatter correction. In this approach we use data from mammography to correct for scatter in tomosynthesis. The current trend is to perform mammography and tomosynthesis with the same system that is capable of performing both tests. Typically, this is implemented by acquiring a tomosynthesis projection sequence either preceding or following a single standard digital radiograph or digital mammogram. During the standard digital radiograph or digital mammogram the anti-scatter grid is in place so as to produce a substantially scatter-reduced image (also referred to as a "reduced x-ray scatter image"). An image produced without using scatter reduction methods will be termed a "full x-ray scatter image." However, during digital tomosynthesis acquisition the anti-scatter grid is moved out of the x-ray beam to ensure that the anti-scatter grid does not cut-off the x-ray beam during projection acquisition at oblique angles. It is expected that one will be able to utilize the "reduced x-ray scatter image" from the digital radiograph or digital mammogram in combination with the "full x-ray scatter image" from the digital tomosynthesis acquisition that is acquired at a projection angle closest to the digital radiograph or digital mammogram to provide an a priori estimate of scatter for that projection angle. Subsequently, estimates for other projection angles of the tomosynthesis acquisition can be inferred using either analytical approaches that are based on pre-determined variation of scatter with projection angle as described in Sechopoulos, I., S. Suryanarayanan, S. Vedantham, C. J. D'Orsi, and A. Karellas, *Scatter radiation in digital tomosynthesis of the breast.* Med Phys, 2007. 34(2): p. 564-76, or using accelerated Monte Carlo based approaches that use the a priori information. The position dependent x-ray scatter estimate for each projection angle thus determined can be used for numerical scatter-correction techniques such as those based on convolution approaches, deconvolution approaches and iterative methods.

An important aspect in our system and method is the use of the digital mammography image at zero-degree projection angle which has reduced scatter due to the presence of an anti-scatter grid, and we deduce the scatter content for the zero-degree tomosynthesis projection, wherein the anti-scatter grid not present. Once the scatter content at zero-degree tomosynthesis projection is determined, the scatter-content at all other tomosynthesis projection angles can be determined using pre-computed or analytically modeled scatter variation with projection angle.

Sparse Stationary X-Ray Source Array

During initial development of the stationary x-ray source array technology, it may not be cost efficient to produce a large number of x-ray focal spots that constitute the array or it may not be feasible to position the x-ray focal spots close enough to provide adequate angular sampling. Hence, it is expected that one can use a sparse stationary source array comprising a few focal spot sources that can be rotated with reference to the object for tomosynthesis projection acquisition. In addition, the use of AABM is expected on such a stationary source array which can also be modulated as a function of its rotation about the object.

An advantage of a sparse satellite x-ray source array is that its use limits the required range of mechanical movement of the x-ray source, which could improve the use of "step-and-shoot" methods. For example, one could acquire multiple projections corresponding to the location of each source position with the satellite array situated in a first position. One could then rotate the array to the next angular position and the process repeated. This can reduce blurring caused by motion vibrations and angular movement of the x-ray source, because fewer angular transits would be required to obtain a full set of images.

Combined X-Ray Tube and Stationary X-Ray Source Array

Currently, stationary x-ray source arrays cannot achieve x-ray fluence rates that are as high as that provided by conventional x-ray tubes. Hence, we describe using a conventional x-ray tube for the central (zero-degree) projection and stationary x-ray source for other oblique projections. The conventional x-ray tube will also be used for standard projection imaging such as digital radiography or digital mammography as conventional x-ray tubes have demonstrated the capacity to provide the necessary x-ray fluence rate for such applications. This approach also enables the virtually concurrent acquisition of a conventional mammographic and tomosynthesis image without repositioning the object being imaged. This allows for improved image fusion between the digital radiograph and digital mammogram with the reconstructed tomographic dataset that is free of spatial misregistration due to repositioning of the object being imaged.

An advantage of using a conventional x-ray tube for the central (zero-degree) projection is that it allows the use of high fluence imaging needed for standard projection imaging such as digital radiography and digital mammography within an acceptable time frame. Also, the described configuration overcomes blurring due to mechanical movement of the x-ray source. In addition the apparatus and method are also suitable for contrast-enhancement imaging of the object or anatomy, with or without the use of dual-energy technique, wherein images are acquired after injection of contrast media such as intravenously injected iodinated contrast. The described approach also allows for the acquisition of rapid stereoscopic views by using two of the satellite sources to acquire two views that can be viewed in stereo mode. Alternatively, the conventional x-ray tube can provide one image, while one of the satellite sources can provide the second image so that a stereoscopic image pair is obtained and can be viewed in stereo mode. Also, the described approach can be used for tissue sampling such as needle-core biopsy using stereotactic localization, wherein at least one of the satellite sources is used to acquire one of the two views. Alternatively, both views for stereotactic localization can be obtained using satellite sources.

Scatter Correction in Digital Tomosynthesis

Currently digital tomosynthesis methods do not use any technique for reducing x-ray scatter such as an anti-scatter grid due to grid-cutoff. However, standard projection imaging methods use an anti-scatter grid to reduce x-ray scatter. The combination of digital tomosynthesis with standard digital x-ray imaging appears to be desirable clinically. In such applications, it is expected that the standard digital x-ray imaging acquired with the anti-scatter grid will provide an estimate of "reduced x-ray scatter image" and that the image acquired at a projection angle closest to the standard digital x-ray imaging during digital tomosynthesis acquisition without the anti-scatter grid will provide an estimate of "full x-ray scatter image." It is expected that these two images at different x-ray scatter conditions can be used to arrive at an estimate of the position-dependent x-ray scatter content for tomosynthesis projection at that projection angle. Position-dependent x-ray scatter content at each tomosynthesis projection angle can then be estimated either analytically using pre-determined numerical methods or using Monte Carlo techniques. Once the position-dependent x-ray scatter content at each projection angle has been estimated, they are used as a priori information for numerical scatter correction techniques that are based on convolution approaches, deconvolution approaches or iterative approaches.

An advantage of this feature is that X-ray scatter correction can provide for improved contrast and can reduce artifacts in the image. We are not aware of any prior art that utilizes scatter information under two conditions, i.e., with and without an anti-scatter grid to obtain scatter estimates for scatter correction.

Apparatus

Figure 7:
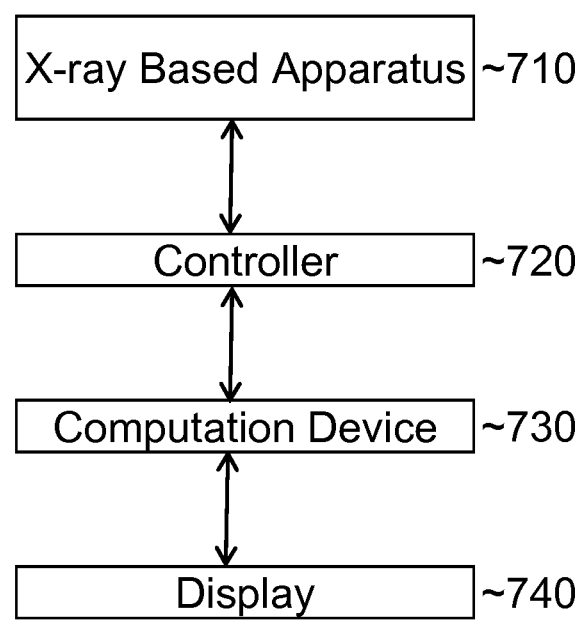
FIG. 7 is a schematic diagram that illustrates the components of an apparatus according to principles of the invention and the interactions among the components.

FIG. 7 is a schematic diagram that illustrates the components of an apparatus according to principles of the invention and the interactions among the components. As illustrated in FIG. 7, an x-ray-based apparatus 710 such as is shown in any of FIG. 1, FIG. 2, FIG. 3, FIG. 4, FIG. 5, or FIG. 6 is provided to perform the positioning of x-ray sources and an object to be examined A controller 720 is provided that communicates bi-directionally with the apparatus 710. The controller 720 controls the activities of the apparatus 710, and receives data from one or more detectors in the apparatus 710. A computational device 730 communicates with the controller 720, to direct the controller to control the apparatus 710, and to receive from the controller 720 data to be process to generate the one of more stereoscopic, radiographic and tomographic images of the object or interest. The computational device 730 is in one embodiment a general purpose programmable computer provided with instructions recorded on a machine readable medium, and includes a memory upon which the data and/or the generated images can be recorded. The computational device 730 communicates with a display 740, which can display one or more generated images to a user. The display can have one or more display screens, and can operate so as to provide a 3-D stereoscopic image if and when such an image is provided for display. The computational device 730 also includes a user interface that permits a user to initiate operation of the apparatus, and permits a user to request that results be provided as any of a displayed image, a recorded image, recorded data, and data and/or images to be provided to a user at a remote location.

Application

The invention described herein is directly applicable to digital breast tomosynthesis and digital chest tomosynthesis, which are considered as highly-promising candidates for clinical success.

Definitions

Recording the results from an operation, data acquisition, or computation, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An x-ray apparatus for making an image, comprising:
   an object holder configured to position an object of interest to allow the making of an image of said object;
   an x-ray source configured to provide a first x-ray beam having a high x-ray fluence rate to illuminate said object of interest along a first axis;
   at least one peripheral satellite x-ray source configured to provide at least one secondary x-ray beam having lower x-ray fluence rate than said fluence rate of said first x-ray beam, said at least one secondary x-ray beam configured to illuminate said object of interest along a respective axis that is angularly displaced from said first axis;
   a detector configured to detect x-ray radiation that has passed through said object of interest from said x-ray source and from said at least one peripheral satellite x-ray source, said detector having an output port configured to provide non-volatile signals representative of said detected x-ray radiation that has passed through said object of interest;
   a controller configured to command the operation of said x-ray source, configured to command the operation of each of said at least one peripheral satellite x-ray source, and configured to command the operation of said detector to generate said non-volatile signals representative of said detected x-ray radiation that has passed through said object of interest; and
   a computation unit configured to receive said non-volatile signals representative of said detected x-ray radiation from said detector and configured to manipulate said non-volatile signals representative of said detected x-ray radiation to provide at least one image of said object of interest, said computation unit configured to perform at least one action selected from the group of actions consisting of recording said image of said object of interest, displaying to a user said image of said object of interest, and transmitting said image to a data handling system.

2. The apparatus for making an image of claim 1, wherein said object of interest is a body part of a living being.

3. The apparatus for making an image of claim 2, wherein said body part of a living being is a human breast.

4. The apparatus for making an image of claim 1, wherein said x-ray source and at least one peripheral satellite x-ray source are configured to be rotated as a combined unit with reference to said object of interest.

5. The apparatus for making an image of claim 1, wherein said x-ray source and at least one peripheral satellite x-ray source are configured to be positioned independently of one another with reference to said object of interest.

6. The apparatus for making an image of claim 1, wherein at least one peripheral satellite x-ray source is configured to be operated individually.

7. The apparatus for making an image of claim 1, wherein said detector is configured to rotate or move laterally to track an x-ray beam.

8. The apparatus for making an image of claim 1, wherein said controller is configured to control a parameter selected from the group of parameters consisting of an x-ray beam energy, an x-ray beam fluence rate and an x-ray beam duration in response to an orientation of said x-ray beam.

9. The apparatus for making an image of claim 1, further comprising an anti-scatter grid located in an x-ray beam path.

10. The apparatus for making an image of claim 1, further comprising a computational unit configured to apply an x-ray scatter correction method.

11. The apparatus for making an image of claim 1, wherein said at least one image of said object of interest is an image selected from the group of images consisting of a radiographic image, a stereoscopic image, and a tomographic image.

12. The apparatus for making an image of claim 1, wherein said x-ray source configured to provide a first x-ray beam having a high x-ray fluence rate is a high power source.

13. The apparatus for making an image of claim 12, wherein said high power source is selected from the group of sources consisting of a rotating anode source, a high fluence field emission source, and a synchrotron.

14. A method of making a plurality of images, comprising the steps of:
providing an object of interest for the purpose of making an image of said object;
illuminating said object of interest with a first x-ray beam having a high x-ray fluence rate, said first x-ray beam propagating along a first axis;
illuminating said object of interest with at least one secondary x-ray beam having lower x-ray fluence rate than said fluence rate of said first x-ray beam, said at least one secondary x-ray beam propagating along a respective axis that is angularly displaced from said first axis;
detecting said first x-ray beam and said at least one secondary x-ray beam after they have each passed through said object of interest;
generating non-volatile signals representative of said detected x-ray radiation that has passed through said object of interest;
manipulating said non-volatile signals representative of said detected x-ray radiation to provide a plurality of images of said object of interest, said plurality of images comprising a stereoscopic image and at least one image selected from the group consisting of a radiographic image and a tomographic image; and
performing at least one action of recording said images, transmitting said images to a data handling system, and displaying said images to a user.

15. The method of making a plurality of images of claim 14, wherein said step of illuminating said object of interest with a first x-ray beam, said step of illuminating said object of interest with at least one secondary x-ray beam, said step of detecting said first x-ray beam and said at least one secondary x-ray beam, and said step of generating non-volatile signals representative of said detected x-ray radiation are performed in response to commands from a controller.

16. The method of making a plurality of images of claim 14, wherein said step of illuminating said object of interest with a first x-ray beam and said step of illuminating said object of interest with at least one secondary x-ray beam are performed in any order.

17. The method of making a plurality of images of claim 14, wherein said step of illuminating said object of interest with at least one secondary x-ray beam includes illuminating said object of interest with a first of said at least one secondary x-ray beams in a first time interval and illuminating said object of interest with a second of said at least one secondary x-ray beams in a second time interval different from said first time interval.

18. The method of making a plurality of images of claim 14, wherein a source of a first of said at least one secondary x-ray beams provides x-ray illumination while a source of a second of said at least one secondary x-ray beams is moving.

19. The method of making a plurality of images of claim 14, wherein at least one of said steps of illuminating said object of interest comprises illuminating said object of interest with an x-ray beam having at least one parameter selected from the group of parameters consisting of x-ray beam energy, x-ray fluence rate and x-ray beam duration, said at least one parameter having a value that is dependent on an orientation of said x-ray beam.

20. The method of making a plurality of images of claim 14, wherein at least one of said steps of illuminating said object of interest with at least one secondary x-ray beam is used to provide one or more of said stereoscopic image, said radiographic image and said tomographic image.

21. The method of making a plurality of images of claim 14, wherein said step of illuminating said object of interest with at least one secondary x-ray beam is used for stereotactic localization to obtain samples of said object of interest.

22. The method of making a plurality of images of claim 14, wherein at least one of said steps of illuminating said object of interest comprises the steps of:
illuminating said object of interest with an anti-scatter grid in an x-ray beam path;
illuminating said object of interest without an anti-scatter grid in said x-ray beam path, and;
applying an x-ray scatter correction method comprising the steps of:
estimating an x-ray scatter present in an image recorded at a first beam orientation;
determining an x-ray scatter present in an image recorded at a second beam orientation different from said first beam orientation by using said estimated x-ray scatter estimated at said first beam orientation; and
applying said determined x-ray scatter as a correction for x-ray scatter in an image recorded at said second beam orientation.

23. The method of making a plurality of images of claim 22, wherein the step of determining an x-ray scatter present in an image recorded at a second beam orientation is performed using Monte Carlo simulations.

24. The method of making a plurality of images of claim 22, wherein the step of determining an x-ray scatter present in an image recorded at a second beam orientation is performed using a library of data that accounts for the range of dimensions and properties of said object.

25. The method of making a plurality of images of claim 22, wherein the step of applying said determined x-ray scatter as a correction is performed using at least one mathematical procedure selected from the group of mathematical procedures consisting of analytical mathematical operations, iterative mathematical operations, convolution techniques and de-convolution techniques.

* * * * *